US007857747B2

(12) United States Patent
Muntermann

(10) Patent No.: US 7,857,747 B2
(45) Date of Patent: Dec. 28, 2010

(54) DEVICE AND METHOD FOR TREATMENT WITH MAGNETIC FIELDS

(76) Inventor: Axel Muntermann, Gotenweg 51, Wetzlar (DE) 35578

(\*) Notice: Subject to any disclaimer, the term of this patent is extended or adjusted under 35 U.S.C. 154(b) by 1631 days.

(21) Appl. No.: 10/479,207

(22) PCT Filed: May 31, 2002

(86) PCT No.: PCT/EP02/05967

§ 371 (c)(1),
(2), (4) Date: Apr. 8, 2005

(87) PCT Pub. No.: WO02/096514

PCT Pub. Date: Dec. 5, 2002

(65) Prior Publication Data

US 2005/0228210 A1 Oct. 13, 2005

(51) Int. Cl.
*A61N 2/00* (2006.01)
*A61N 2/02* (2006.01)
*A61N 2/04* (2006.01)

(52) U.S. Cl. .................. 600/15; 600/9; 600/13
(58) Field of Classification Search ............ 600/9–15
See application file for complete search history.

(56) References Cited

U.S. PATENT DOCUMENTS

| | | | | |
|---|---|---|---|---|
| 3,568,047 | A | * | 3/1971 | Look et al. .................. 324/307 |
| 4,468,621 | A | * | 8/1984 | Hinshaw .................... 324/309 |
| 4,528,509 | A | * | 7/1985 | Radda et al. ................ 324/309 |
| 4,573,015 | A | * | 2/1986 | Abe et al. .................. 324/309 |
| 4,695,799 | A | * | 9/1987 | Hardy et al. ................ 324/307 |
| 5,224,922 | A | * | 7/1993 | Kurtz ....................... 600/13 |
| 5,359,289 | A | * | 10/1994 | van der Meulen ........... 324/320 |
| 5,410,249 | A | * | 4/1995 | Van Yperen et al. ........ 324/309 |
| 5,441,495 | A | | 8/1995 | Liboff et al. |
| 5,619,139 | A | * | 4/1997 | Holczer et al. ............. 324/318 |
| 5,725,558 | A | | 3/1998 | Warnke ..................... 607/3 |
| 6,461,289 | B1 | * | 10/2002 | Muntermann ............... 600/9 |

(Continued)

FOREIGN PATENT DOCUMENTS

DE 2821114 11/1978

(Continued)

OTHER PUBLICATIONS

Buchthal S, den Hollander J. Abnormal myocardial phosphorus-31 nuclear magnetic resonance spectroscopy in women with chest pain but normal coronary angiograms. New England Journal of Medicine 342 (12): 829-35, 2001.*

(Continued)

*Primary Examiner*—Charles A Marmor, II
*Assistant Examiner*—Catherine E. Burk
(74) *Attorney, Agent, or Firm*—Ohlandt, Greeley, Ruggiero & Perle, LLP

(57) ABSTRACT

The invention relates to a device for treatment with magnetic fields, which provides an easily transportable and storable device for the treatment with magnetic fields, which is also convenient for patients and in particular is economical to produce. The device comprises: a first device for generation of a first magnetic field, a second device for generation of a second magnetic field and a support with an upper side and a lower side, whereby the support is embodied for applying the treated body regions of the patient thereto.

11 Claims, 8 Drawing Sheets

U.S. PATENT DOCUMENTS

| | | | |
|---|---|---|---|
| 6,558,311 B1 * | 5/2003 | Muntermann | 600/13 |
| 2001/0005912 A1 * | 7/2001 | Duerr | 5/601 |
| 2005/0218894 A1 * | 10/2005 | Miyawaki et al. | 324/309 |

FOREIGN PATENT DOCUMENTS

| | | |
|---|---|---|
| DE | 4004682 | 8/1991 |
| DE | 4026175 | 2/1992 |
| DE | 198 27 736 | 12/1999 |
| EP | 0 392 626 | 10/1990 |
| EP | 0 661 079 | 7/1995 |
| JP | 53 148191 | 12/1978 |
| WO | WO82/03178 | 9/1982 |
| WO | WO 91/15263 | 10/1991 |
| WO | WO 9966986 A * | 6/1999 |
| WO | WO 99/66986 | 12/1999 |

OTHER PUBLICATIONS

Froboese et al., "Evaluation of the effectiveness of three-dimensional pulsating electromagnetic fields of the MultiBioSignal Therapy (MBST) in respect to the regeneration of cartilage structures," Orthopaedische Praxis 8/200, 36. Jahrgang, pp. 510-515.

A treatment for cartilage regeneration—First scientific study of the therapeutic applicability of nuclear magnetic resonance singnals (MBST—NuclearMargenticResonanceTherapy) to cartilage structures in vivo!, 4 pages.

Christian Thuile, Das große Buch der Magentfeldtherapie, Neomedica GmbH, 1997, p. 355.

Search Report for corresponding European Patent Application No. 06025428.1-2319 dated Mar. 12, 2008.

GMW Associates, "Virginia Scientific Digital NMR Teslameter, FW101," http://www.gme.com/magnetic_measurements/VSI/FW101.html.

* cited by examiner

90° Puls    180°Puls    Echo

Echo, B = 23,4Gs

Echo, B = 23.2 Gs

Echo, B = 23.8 Gs $t = t_0$ $t = t_1 > t_0$ $t = t_2 > t_1$

DEVICE AND METHOD FOR TREATMENT WITH MAGNETIC FIELDS

This application claims priority in PCT International Application No. PCT/EP02/05967, filed May 31, 2002, and German Application No. DE 201 09 058.9 filed on May 31, 2001, the disclosures of which are incorporated herein by reference.

FIELD OF THE INVENTION

The invention relates to an apparatus and a method for treatment with magnetic fields in general, and to the influencing of spins and/or magnetic moments in tissue to be treated, in particular.

BACKGROUND OF THE INVENTION

Non-invasive treatment methods are finding ever more new fields of application in the medicine. With respect to the invention registered here, apparatuses and methods for therapeutic treatment by means of external magnetic fields should be mentioned in particular. Even though, until now, the precise mechanism of operation of such therapies has not been understood in detail, their therapeutic success has been scientifically proven and is generally recognized. Investigations into the results of known magnetic field therapies can be found, for example, in "Orthapädische Praxis" August/2000, [Orthopedic practice] year 36, pages 510 to 515 and in Fritz Lechner, "Elektrostimulation und Magnetfeld-therapie. Anwendung, Ergebnisse und Qualitätssicherung" 1989 ["Electrostimulation and magnetic field therapy. Use, results and quality assurance"].

In particular, it has been found in investigations such as these that magnetic field therapies applied to patients in some cases produce considerable improvements in the signs and symptoms without significant negative side effects that can be verified. A further major advantage of magnetic field therapies is that an operation which is associated with considerable pain, risks and costs for the patient may possibly be completely avoided.

By way of example, DE 40 26 173 discloses an apparatus which produces pulsed and modulated magnetic fields in order to treat patients. In this case, body tissue is subjected to a magnetic field which is produced by superimposition of a constant magnetic field and a magnetic alternating field.

Pulsed magnetic fields are typically produced by means of a pulsed current, which flows through a coil. However, pulsed fields such as these in coils require a large amount of energy and have a high degree of inertia since the coil inductance slows down the rate of change of the field.

The healing effect of this magnetic field therapy comprises, inter alia, the relief of osteoporosis and the consequences of a stroke. In this, it appears to be probable that the magnetic fields which are applied promote transport and/or metabolism processes which lead to a positive therapeutic effect. Until now, it has been assumed that the positive therapeutic effect is caused by an energy interchange between fields and components of cells (protons, ions etc.). In this case, the energy transfer has been explained by the stimulation and/or absorption of ion-cyclotron resonances (ICR) in a biological body, and appropriate, ICR conditions are thus looked for. The known apparatuses are consequently based on production of ICR conditions.

However, this causal explanation appears to be questionable in some circumstances, since cyclotron resonances generally occur only on free particles, for example in a vacuum or in the case of electrons in the conductance band of a semiconductor. Furthermore, simple calculation can also be used to show that a cyclotron movement will be carried out on an orbit whose radius is intrinsically greater than the average diameter of a cross section of a human body. This means that an explanation with regard to energy transfer for cyclotron resonance may be questionable, particularly for solid tissue.

It is also possible for the effect to be based on piezoelectric processes in the body. This explanation approach is based on the assumption that there is an electrical field around every body joint and, in the healthy state, every movement causes a piezo voltage, since the cartilage has piezoelectric characteristics. In the unhealthy state, these piezo voltages could be simulated by induced voltages. In this context, see also Christian Thuile, "Das große Buch der Magnetfeldtherapie", Linz 1997. [The Big Book on magnetic field therapy].

A further apparatus for treatment of a biological body with magnetic fields, which produces spin resonances within the body to be treated, is disclosed in Laid-Open Specification WO 99/66986 from the same applicant. This apparatus as described in Laid-Open Specification WO 99/66986 is, however, essentially based on carrying out specific reproducible treatment with magnetic fields in all biological materials, irrespective of whether any ionic parts are present. The cited apparatus. achieves the positive therapeutic effects by production of spin resonances and spin resonance sequences. In this case, the nuclear magnetic resonance is, however, also used in particular for energy transfer. In other fields of technology, nuclear magnetic resonance methods (so-called NMR methods) have already been known for a long time. They are used in particular for medical diagnosis and in general for the high-precision magnetic field measurement. With regard to the latter application, reference should be made, for example, to the "Virginia Scientific FW101 Flowing Water NMR Teslameter".

It should also be stated that the known apparatuses for therapeutic medicine generally comprise large coil systems with which the magnetic fields are generated and varied. However, these coil systems have a high inductance, which leads to long switching time constants and to consumption of a large amount of energy. Long switching times disadvantageously lead, however, to poor efficiency with regard to dynamic processes in the body.

Furthermore, the coil systems are typically designed such that they have openings into which body parts, for example, arms or legs, can be inserted. In consequence, the known apparatuses are relatively shapeless and have disadvantages with regard to the possible ways to store them and transport them. Apart from this, in some cases, they are not convenient for the patient. Furthermore, the energy required for the most known apparatuses is very high, since the coil systems produce strong magnetic fields.

In addition, there are still a number of open questions with regard to the physical-physiological way in which the apparatuses operate and with regard to the processes which are initiated by them in the body. However, in the past, without any detailed knowledge of the way in which they operate, an optimized design and the optimum parameters for its operation could be determined only with difficulty.

One object of the present invention is thus to provide an improved apparatus and an improved method for treatment with magnetic fields.

A further object of the invention is to make an apparatus and a method available by means of which electromagnetic stimuli which are produced by movement in the body, in particular the natural behavior of magnetic moments in the body can be modeled or simulated artificially during movement in the earth's magnetic field.

Another object of the invention is to make available an apparatus and a method which allow short switching time constants and consume little energy.

A further object of the invention is to make available an apparatus for treatment with magnetic fields, which can be transported and stored easily, is convenient for the patient and, in particular, can also be manufactured at low cost.

The invention is based on the extremely highly surprising knowledge that positive therapeutic effects from treatment with magnetic fields can be traced back to movement simulation via spin resonance signals.

Magnetic moments, for example electron and nuclear spin moments can be aligned just in the earth's magnetic field in a human, animal or other biological body, and thus produce macroscopic magnetization. Any movement of a body part leads to a small change in the direction of this magnetization. Provided that the magnetization direction is not aligned parallel to the earth's magnetic field direction, the magnetization precesses at a frequency of about 2000 Hz in the earth's magnetic field, and induces an alternating voltage at the same frequency in the environment. This induced voltage can be measured using an external coil, and is in the milli volt range. However, the induced voltage in the body is considerably greater since the distances are shorter. The human nervous system registers this voltage and thus identifies the movement. In consequence, the metabolism is activated since energy is required for muscular work.

Various debilitations restrict the movement of a patient and his or her metabolism. The apparatus according to the invention and the method result in predetermined and deliberate rotation of the spins and of the macroscopic tissue magnetization that is produced by the spins. With regard to the spin resonances which are produced naturally by the earth's magnetic field in the body, the organism is made to believe that movement has taken place, which has not taken place in reality. To do this, the apparatus according to the invention produces suitable magnetic fields which vary the alignment of the spins and/or of the magnetization in such a way that this simulates a movement of the body area which is arranged in the treatment area. In this context, it has been possible, inter alia, by the use of the present invention, to achieve very good treatment success in the therapy for osteoporosis.

A first embodiment of the invention is distinguished in that the apparatus according to the invention for treatment with magnetic fields comprises a first and a second device for production of a first and a second magnetic field, respectively, and a mount, in particular a mat for body areas of a patient to be treated, or the entire patient, to rest on and/or against. In this case, the mount, such as the mat defines an upper face and a lower face, between which the first and second devices for production of the first and second magnetic fields, respectively, are preferably arranged. This arrangement allows a very compact, in particular very flat, configuration.

In addition to a mat in which the devices for production of the first and second magnetic fields are arranged, a treatment couch or a treatment stool may also be used as the mount. In addition, systems are possible which are placed on the patient, or on the tissue to be treated. By way of example, the mount may comprise a multi-winged arrangement which can be placed around a body part, in particular the head, of a patient and is placed against the head of a patient. This apparatus may, for example, comprise two or more wings whose sizes are such that they can be placed around both ears or around the jaw of a patient. In particular, with this form of mount, the first and second devices for production of the first and second magnetic fields, respectively, can also be integrated in two or more or all of the wings.

Furthermore, the mount may also be in the form of leggings, which can be placed around the legs or arms, for example.

Amount which comprises a cover may also be advantageous for certain applications. For the treatment of animals, for example, inter alia such as horses, the cover can be placed over the animal for treatment.

The apparatus is characterized in that the mount comprises a treatment couch and/or a treatment stool and/or a multi-winged arrangement which can be placed around a body part, in particular the head, of a patient, and/or leggings and/or a cover.

As is clear from the above examples, there are accordingly no limits to the shape and condition of the mount, which can be matched appropriately to the purpose.

The atomic nuclei in the patient's tissue define a spin resonance frequency, or have such a frequency, in the magnetic fields. In this case, the resonant frequency is correlated to the field strength of the magnetic field. For example, the following equation applies to hydrogen atoms:

$$F[\text{kHz}] = 4.225 \times B[\text{Gauss}],$$

where F is the nuclear magnetic resonance frequency in kilohertz, and B is the magnetic field strength in gauss. For example, the nuclear magnetic resonance frequency is 16.9 kHz for a magnetic field of 4 gauss.

The second device is preferably designed to produce an alternating field. The two devices for production of the first and second magnetic fields in this case form, in particular, a classical arrangement for production of nuclear magnetic resonance. In this case, the second magnetic field preferably oscillates at the spin resonance frequency, which is defined essentially by the nature of the particles, elements or chemical compounds in the body and by the strength of the first magnetic field. The spin resonance frequency that is produced is preferably between 1 kHz and 1 MHz, particularly preferably between 2 kHz and 200 kHz, and most preferably in the region of about 100 kHz.

A preferred embodiment in which the first and second devices are arranged in a plane which runs parallel to the plane of the mat is particularly advantageous. In this case, the first and/or second devices can preferably be arranged completely within the mat, between its upper face and lower face. This results in a particularly simple and practical embodiment, in which the patient simply lies on the mat for treatment. This arrangement in a plane also provides a planar geometry, in which mutually orthogonal magnetic fields can nevertheless be produced in the treatment area.

The apparatus can be stored and transported particularly easily if, according to one preferred embodiment, the mat can be folded once or more by subdivision into two or more sections. In this case, the first and second devices are preferably accommodated in the same section of the mat. The mat preferably has a thickness of about 3 to 10 cm, a width of 70 cm and a length of 210 cm, so that, when it is folded twice by way of example, dimensions of about 9 to 30 cm by 70 cm by 70 cm are achieved.

The second device preferably comprises a toroidal coil. This defines a coil plane in which the windings run, and a coil axis which is at right angles to the coil plane. As will be obvious to those skilled in the art, a magnetic field in the direction of the coil axis is essentially produced in the center of the coil. In the direction of the coil axis, the coil or second device has an extent of less than 50 cm, preferably of less than 20 cm, and particularly preferably of less than 10 cm, and most preferably of between about 2 cm and 6 cm. The coil or second device has a round to oval or elongated shape with semicircular end areas in the coil plane. In particular, the extent of the coil in the direction of the coil axis is preferably less than the extent of the coil plane, being less than it at least by a factor of 2 or particularly preferably by at least a factor of 5. The special shape makes it possible, in particular, for it to be accommodated completely in the flat mat by producing a highly effective magnetic field at the same time, which is generally not possible with the known large coil arrangements.

The first device preferably comprises at least one, two, three or particularly preferably four coils, with each of these coils preferably being combined with a fixed magnet, for example composed of a ferrite material. This advantageously results in the production of a strong constant basic magnetic field through the ferrite material, with an additional magnetic field which varies with time being superimposed on it, produced by the coils.

It is thus possible to work with relatively small coils and little energy consumption, with an effective magnetic field at the same time.

In one preferred development, the first and second devices for producing the first and second magnetic field, respectively, are arranged in a plane which runs parallel to the plane of the mat surface and the coil plane of the second device. If the first device has two or more coils and/or fixed magnets, the second device is preferably arranged centrally between them.

In particular, the treatment field comprises at least one superimposition of the first and second magnetic fields. In the treatment area above the mat surface, in particular where a patient is located or is lying for treatment, the magnetic lines of force which are produced by the first device run essentially parallel or at least at an acute angle in the range from 0° to 300 or from 0° to 45°, to the mat surface, and/or at right angles or at least at an obtuse angle in the range from 45° or 60° to 120° or 135° to the magnetic lines of force of the second device. The second magnetic field preferably runs at an angle in the range from 30° to 150°, particularly preferably in the range from 45° to 135°, and particularly preferably in the range from 60° to 120°, and most preferably essentially at right angles to the mat surface.

In one embodiment of the invention, the treatment field can be varied with time such that the alignment of the spins or of the macroscopic magnetization which is produced by the spins can be varied by means of the variation of the treatment field with time so as to make it possible to simulate a movement of the body area that is arranged in the treatment area, in the earth's magnetic field.

The first magnetic field preferably comprises an essentially parallel superimposition, or parallel superimposition in other directions, of a preferably constant third magnetic field, which is preferably produced by the fixed magnets or ferrites, and of a fourth magnetic field, which preferably varies with time and is preferably produced by auxiliary coils associated with the fixed magnets. In this case, the strength of the third magnetic field is preferably 0.5 gauss to 500 gauss, preferably from 10 gauss to 50 gauss, and particularly preferably in the range from 23 gauss to 24 gauss. The fourth magnetic field, which may also be referred to as the modulation field, oscillates periodically and preferably regularly between preferably −10 gauss and +10 gauss, preferably between −1 gauss and +1 gauss, and particularly preferably between −0.5 gauss and +0.5 gauss, with the latter corresponding approximately to the strength of the earth's magnetic field. It is obvious to those skilled in the art that the third magnetic field represents a constant basic field, and the fourth magnetic field represents amplitude modulation of the first magnetic field.

The fourth magnetic field preferably describes a triangular or sawtooth, waveform oscillation which is symmetrical about 0 gauss, so that the first magnetic field oscillates about the value of the third magnetic field or constant basic field. In consequence, the first magnetic field is preferably amplitude-modulated with a triangular waveform. The mathematical resonance condition is in this case satisfied precisely at the point at which the fourth magnetic field disappears. The strength of the third magnetic field is in this case at least 4 times, 10 times or 20 times as great as the maximum strength of the fourth magnetic field.

If the second magnetic field, as an alternating field and at a frequency which corresponds to the spin resonance frequency of the particles in the tissue in the third magnetic field, is now injected essentially at right angles to the first magnetic field, then this corresponds to an arrangement for producing a so-called fast adiabatic run.

The second magnetic field or alternating field preferably has different intensities during the rising and falling flanks of the first magnetic field. The second magnetic field is particularly preferably injected during the falling flank of the first magnetic field, and is switched off during the falling flank, or vice versa. As a consequence, the spins or the macroscopic magnetization during the "on time" of the second magnetic field are rotated adiabatically away from the direction of the basic field, and relax back again during the "off time" of the second magnetic field.

The frequency of the fourth magnetic field or of the amplitude modulation of the first magnetic field is thus preferably matched to the spin lattice relaxation time of the particles in the tissue. This leads to a preferred period duration of the modulation of the first magnetic field of 1 ms to 10 s, preferably 10 ms to 1 s, and particularly preferably in the region of 200 ms.

As an alternative to the arrangement for a fast adiabatic run, the second magnetic field or alternating field is injected in a short pulse, for example a so-called 90 pulse or a 180° pulse.

The invention will be explained in more detail in the following text using preferred embodiments and with reference to the drawings.

DETAILED DESCRIPTION OF THE INVENTION

Nuclear magnetic resonance makes it possible to vary the magnetization direction in the body without the body being in motion in the process, since the induced nuclear magnetic resonance voltage simulates the body's own movement process. The apparatus and the method according to the invention can thus be used to carry out a therapy which stimulates or speeds up the metabolism.

Figure 1A:
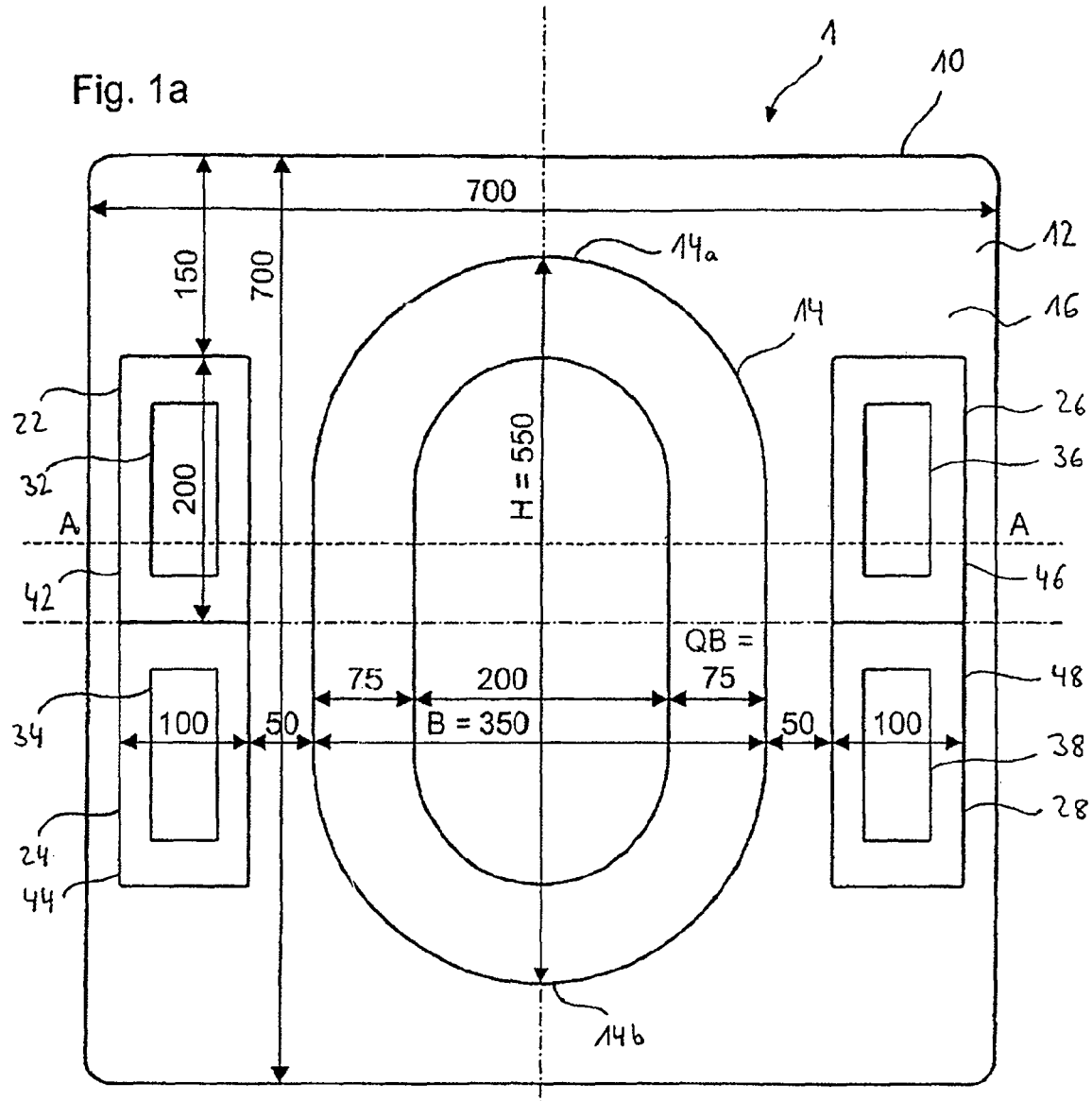
FIG. 1a shows a view of a first embodiment of the invention with the dimensions in mm.
Figure 1B:
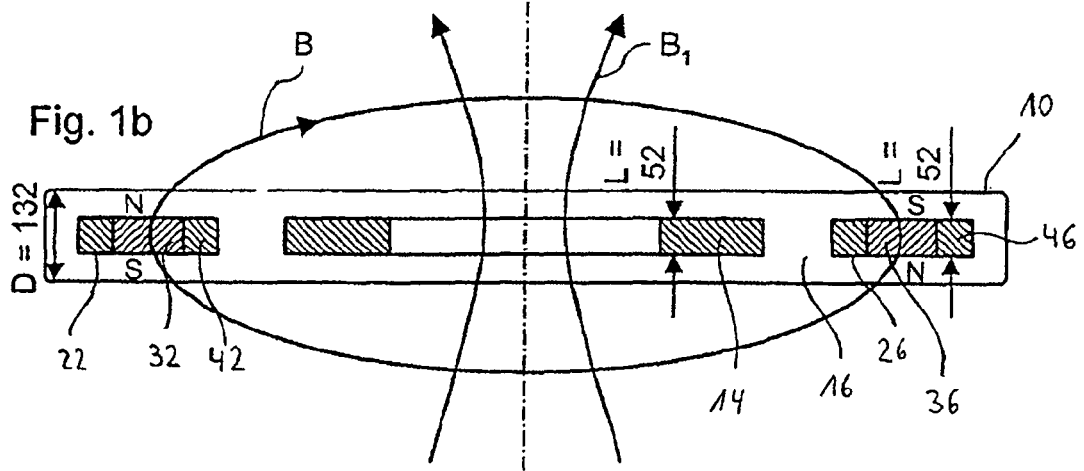
FIG. 1b shows a section drawing along the section line A-A in FIG. 1a with the dimensions in mm.

FIGS. 1a and 1b show a first embodiment of the invention, in which the illustrated dimensions shall be regarded as being only by way of example. The apparatus 1 according to the invention comprises a mat 10 which is subdivided into three sections and can be folded, of which only the central section 12 is illustrated, extending in the plane of the drawing. A second device, at right angles to the plane of the drawing and in the form of a flat toroidal coil 14, is embedded in the section 12 of the mat 10 in order to produce a second magnetic field in cushioning 16 composed of a flexible material, for a example a foam material. The toroidal coil or transmission coil 14 extends in the plane of the drawing with a width of about B=350 mm and a height of about H=550 mm, with the head ends 14a, 14b each being designed to be semicircular. The length of the coil at right angles to the plane of the drawing is about L=52 mm. The cross section through the coils is defined by the length L and a cross-sectional width of about QB=75 mm. The thickness of the mat is about D=132 mm, with the toroidal coil being arranged centrally in the mat, so that cushioning 16, which is also about 40 mm, is in each case arranged between the mat upper face and lower face. There are two devices 22, 24, 26, 28 in each case to the left and to the right of the coil in order to produce a first magnetic field, and these each comprise a fixed magnet 32, 34, 36, 38 and an auxiliary coil 42, 44, 46, 48 in each case, which surround the fixed magnets in the mat plane. Each device 22, 24, 26, 28 has a height of about 200 mm, a width of about 100 mm and a length L at right angles to the plane of the drawing of about 52 mm. The devices 22, 24, 26, 28 are each separated by about 50 mm from the toroidal coil 14 in the direction of the width, and two of the devices 22 and 24 as well as 26 and 28 are in each case adjacent to one another in the vertical direction.

90° Nuclear Magnetic Resonance Signal Pulsed Method

As has already been stated above, a first embodiment of the invention uses a pulsed method, which will be described in detail in the following text.

The molecules or macromolecule complexes of our body are made up predominantly of hydrogen atoms, for example in water ($H_2O$) or in organic molecules (for example in $CH_2$ or $CH_3$). The cores or ions of the hydrogen are protons.

Figure 2:
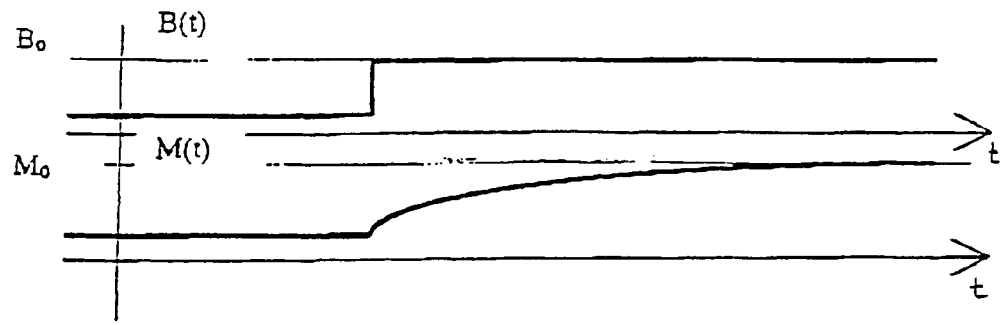
FIG. 2 shows a time profile of a magnetic field B(t) and of the resultant macroscopic magnetization M(t)

Protons have a magnetic moment and a spin (obviously a torque) with a ratio γ (gyromagnetic factor) between them. For protons, $\gamma = 2.67522 \cdot 10^8 T^{-1} s^{-1}$. A steady-state magnetic field $B_0$, for example the earth's magnetic field, produces macroscopic magnetization M(t) exponentially over time with a time constant $T_1$. This is defined by:

$$M(t) = M_0(1 - e^{-t/T_1})$$

where $$M_0 = \chi B_0$$

where $T_1$ is the spin lattice relaxation time and $M_0$ is the asymptotic value of the magnetization. The time profile of the magnetization M(t) which is produced by a sudden application of a magnetic field $B_0$ which is constant after the rise is illustrated in FIG. 2. For protons or hydrogen in human tissue:

$$T_1 = 10s \ldots 10^{-3} s.$$

A spin echo measurement is preferably carried out before the therapeutic treatment, in order to determine the spin lattice relaxation time.

Figure 3:
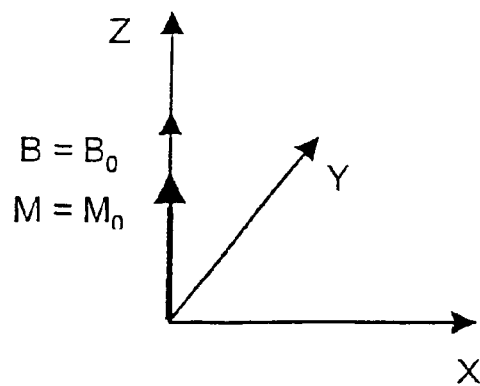
FIG. 3 shows an illustration of the alignment of macroscopic magnetization M in a constant magnetic field $B_0$.

The macroscopic magnetization M is aligned asymptotically parallel to applied magnetic field $B = B_0$, as is illustrated in FIG. 3. FIG. 3 also shows a rectangular and right-handed coordinate system XYZ, which is used as the basis of the orientation for the following analysis.

Microscopically and as required by quantum mechanics, all of the proton spins carry out a precession movement about $B_0$ at a frequency $f_0$. This frequency is referred to as the Larmor frequency. The Larmor frequency $f_0$ is determined as follows:

$$f_0 = \frac{\omega_0}{2\pi}.$$

From this, in the earth's magnetic field, that is to say for $B_0 = 0.5$ Gauss $= 5 \cdot 10^{-5} T$ $$f_0 = \frac{\gamma B_0}{2\pi} = \frac{2,67522 \cdot 10^8 \cdot 5 \cdot 10^{-5}}{2\pi} \text{ Hz} = 2128,872 \text{ Hz}$$

In the earth's magnetic field, the Larmor frequency for protons is in consequence about 2 kHz. The Larmor frequency is also varied only very slightly by the chemical bonds.

Figure 5:
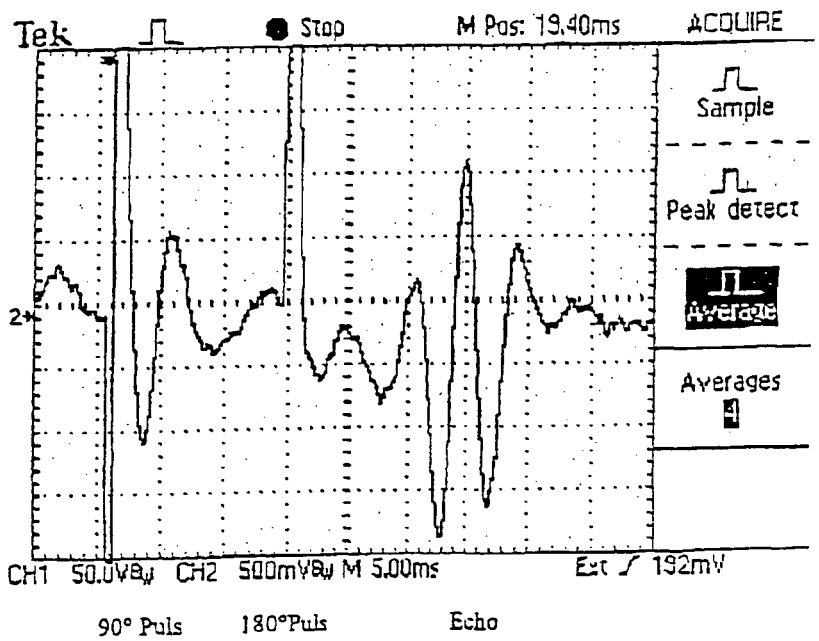
FIG. 5 shows an oscilloscope print-out of a nuclear magnetic resonance signal with phase-sensitive detection using a 100 kHz reference.
Figure 6:
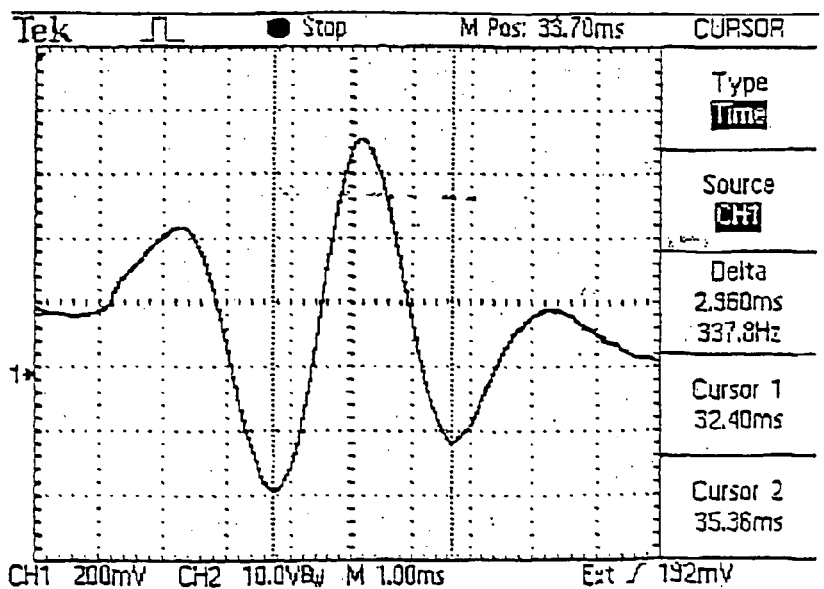
FIG. 6 shows a time detail of a nuclear magnetic resonance signal for $B_0$=23.4 gauss.
Figure 7:
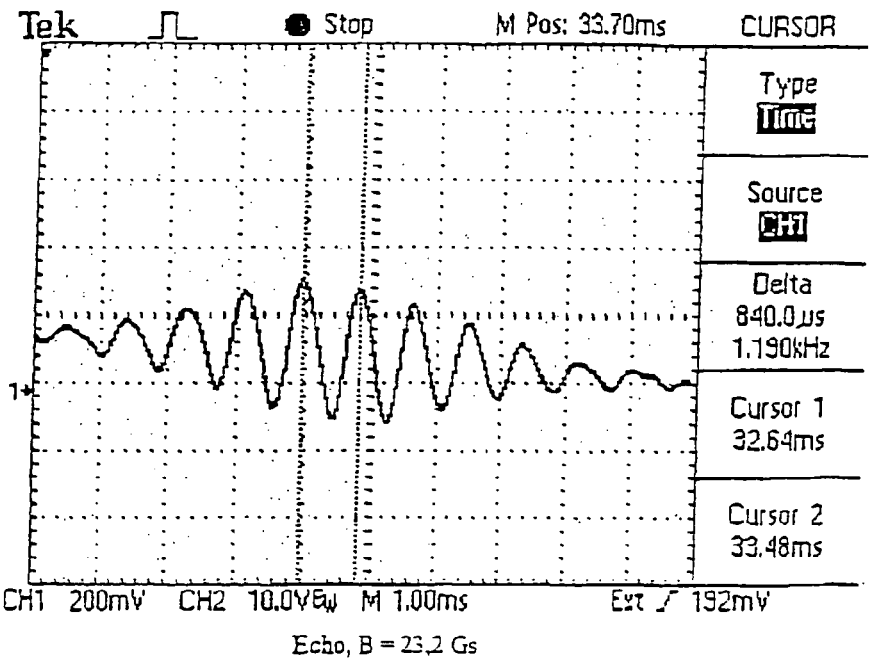
FIG. 7 shows a time detail of a nuclear magnetic resonance signal for $B_0$=23.2 gauss.
Figure 8:
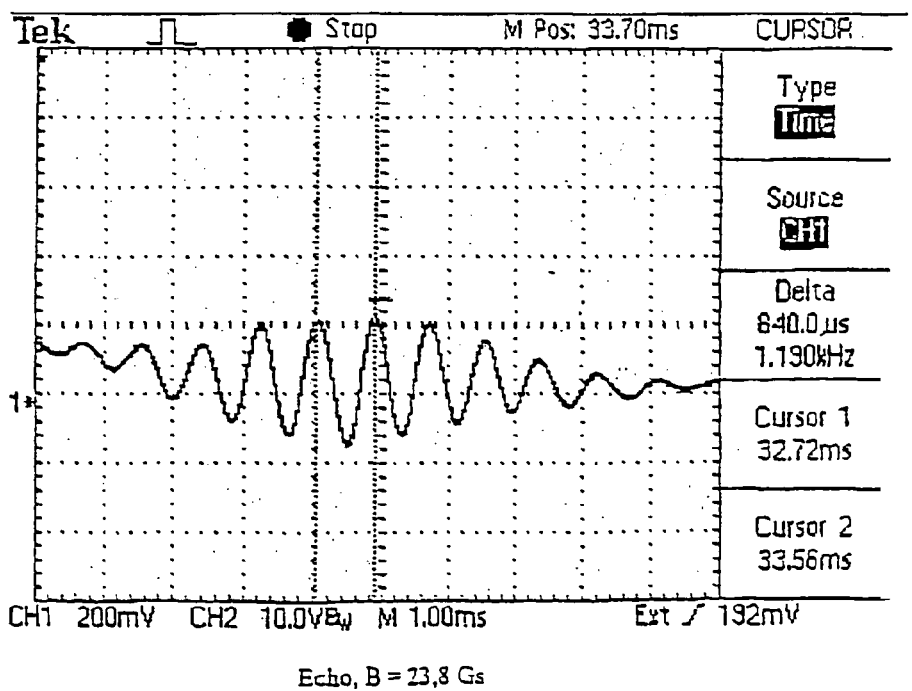
FIG. 8 shows a time detail of a nuclear magnetic resonance signal for $B_0$=23.8 gauss.

FIG. 5 shows an oscilloscope print-out for experimental verification of the Larmor frequency by means of a spin echo measurement with 500 ml of water at 100 kHz and using a 23.5 gauss spectrometer. A 90° pulse and a 180° pulse are injected, and the spin echo is detected. FIGS. 6 to 8 show the spin echoes for a first magnetic field B=23.2 gauss, 23.4 gauss and 23.8 gauss on an enlarged time scale. The first magnetic field B is produced by parallel superimposition of a constant magnetic field $B_0$, by means of the four fixed magnets which are in the form of ferrite magnets 32, 34, 36, 38, and of a magnetic field $\Delta B_0$, which varies with time, produced by the four auxiliary coils 42, 44, 46, 48.

Figure 9:
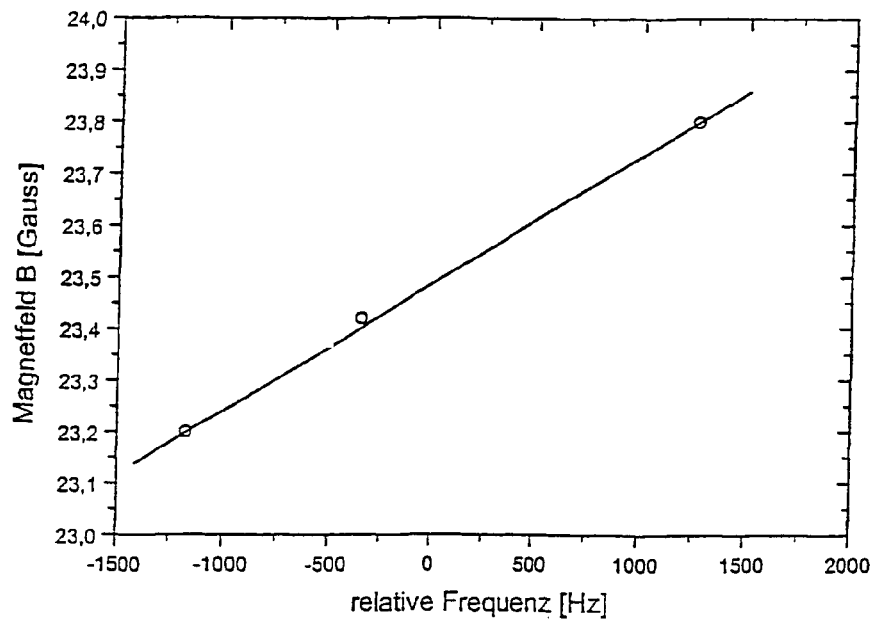
FIG. 9 shows a profile of the magnetic field strength as a function of the relative frequency.

FIG. 9 illustrates the three measurement points from FIGS. 6 to 8 in the form of a graph of the magnetic field in gauss as a function of the relative frequency in Hz. The straight line is a linear interpolation through the measurement points. The relative frequency represents the frequency error from the resonant frequency $f_0$, which is defined by the basic field $B_0 = 23.5$ gauss.

The apparatus according to the invention comprises a flat coil or transmission coil 14 for producing the second magnetic field in the form of a magnetic alternating field $B_1$ at a frequency $f_o$ of about 100 kHz. This frequency corresponds approximately to the Larmor frequency of protons in a mean magnetic field of B=23.5 gauss.

For this purpose, the transmission coil 14 is preferably connected in a very simple manner to a capacitor in order to form a resonant circuit. The resonant frequency of the resonant circuit $f_{LC}$ is $$f_{LC} = \frac{1}{2\pi\sqrt{LC}},$$

where L is the inductance of the transmission coil 14, and C is the capacitance of the capacitor.

If the body areas of a patient or of biological tissue are located in the first magnetic field B, which initially has a constant strength of $B_0$=23.5 gauss, the macroscopic magnetization M of the tissue is the vector sum of the nuclear spins parallel to $B_0$, when $B_0$ in this embodiment runs parallel to the Z-axis (see FIG. 3).

A nuclear magnetic resonance method is now used to deflect the magnetization M away from the $B_0$ direction. Nuclear magnetic resonance changes the magnetization direction, even though the body is at rest. The induced voltage produces an effect as if the body were in motion. Nuclear magnetic resonance can then be used to carry out therapy by stimulating the metabolism.

Figure 4:
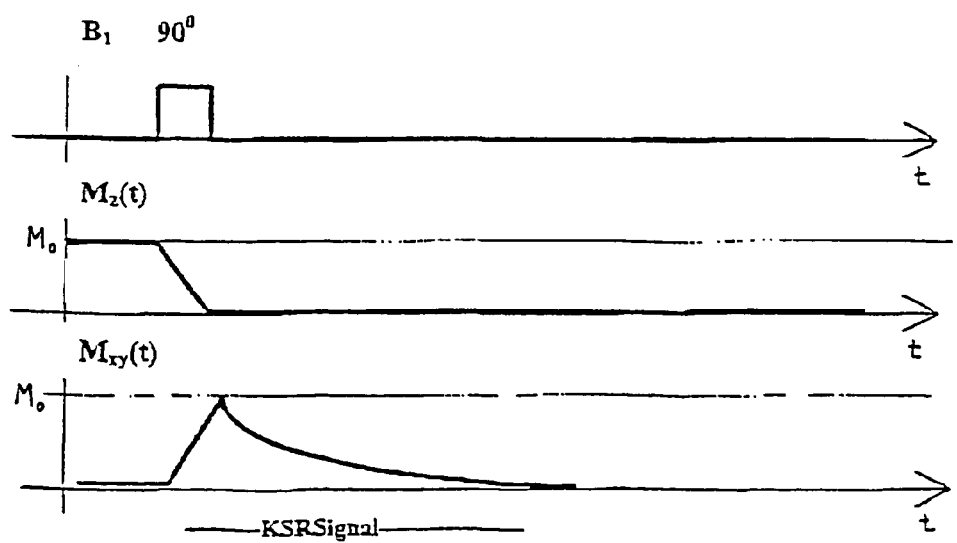
FIG. 4 shows a time profile of a magnetic field B(t) and of the resultant magnetization components $M_z(t)$ and $M_{xy}(t)$ when a 90° pulse is injected.

A so-called 90° radio-frequency pulse is used to rotate the magnetization through 90°. The time profile of the magnetic field and of the magnetization components $M_z(t)$ and $M_{xy}(t)$ is shown schematically in FIG. 4. The transmission coil, whose axis runs parallel to the X axis, generates a rotating radio-frequency field $B_1$, or one which oscillates linearly in the X direction. The macroscopic magnetization M rotates at a frequency $f_1$ about the X axis from the positive Z direction to the X-Y plane. In this case:

$$f_1 = \omega_1/2\pi$$

where $$\omega_1 = \gamma B_1$$

The angle α through which M rotates is:

$$\alpha = \omega_1 t.$$

For a 90° rotation, that is to say $\alpha=\pi/2$, the time duration of the 90° pulse $t_{90}$ is calculated to be:

$$t_{90} = \frac{\pi}{2}\frac{1}{\gamma B_1}.$$

The macroscopic magnetization M is in the direction Y after injection of the 90° pulse. It rotates at $\omega_0$ about the Z axis and induces a voltage in the radio-frequency coil, which can be measured as a nuclear magnetic resonance signal. This signal decays exponentially with the time constant $T_2^*$, and:

$$M_{xy} = M_0 \cdot e^{-t/T_2^*}$$

For a homogeneous magnetic field B: $T_2^* \cong T_2$,
where $T_2$ is the spin-spin relaxation time.
For a less homogeneous magnetic field B: $T_2^* < T_2$
For liquids: $T_1 \cong T_2$ Typical values for $T_2$ are:
Tap water: $T_2 \cong 3s$
Distilled water: $T_2 \cong 30$ s to 3 min
Human tissue: $T_2 \cong 10$ ms to 1 s
Tissue of a hand: $T_2 \cong 100$ ms to 1 s.

Fast Adiabatic Nuclear Magnetic Resonance Run

Figure 10A:
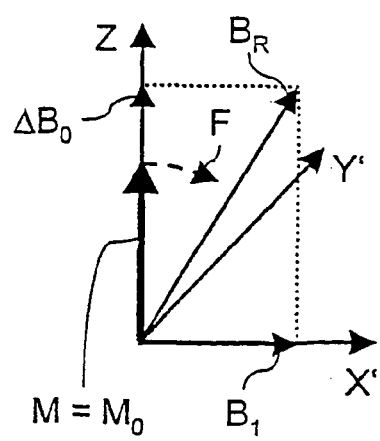
FIG. 10a shows a schematic illustration of the spatial alignment of magnetic fields for a fast adiabatic run at the time $t_0$.
Figure 10B:
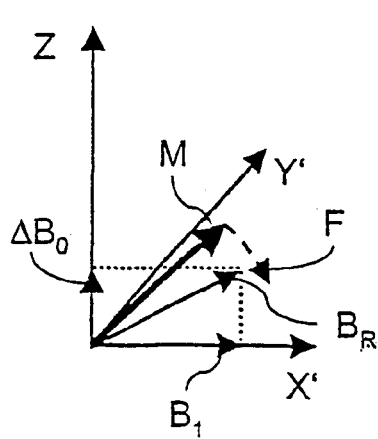
FIG. 10b is as FIG. 10a, but for the time $t_1$ instead of $t_0$.
Figure 10C:
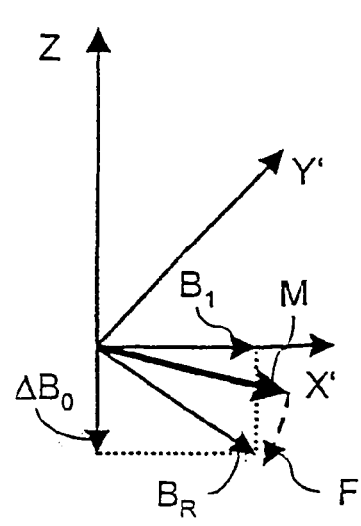
FIG. 10c is as FIG. 10a, but for the time $t_2$ instead of $t_0$.

With reference to FIGS. 10*a* to 10*c* and, alternatively, the pulsed method described above, specific rotation of the magnetization is achieved by means of a fast adiabatic run, which is described in the following text. This is achieved by a field variation of the first magnetic field B or a frequency variation of the alternating field $B_1$, in which case the magnetization M can be rotated from 0 to 180° with respect to the Z axis.

The following magnetic fields are defined in a coordinate system (X' Y' Z) which rotates at $\omega_0$ about the Z axis:

$$\Delta B_0 = B - B_0 \text{ where } B_0 = \omega_0/\gamma$$

$B_1$ and
$B_R$.

In this case, $B_1$ is an alternating field or radio-frequency field which is produced by the transmission coil 14 and, at the time $t=t_0$, runs parallel to the X' axis in the coordinate system X'Y'Z. $B_R$ is the magnetic field or treatment field which results from the superimposition of B and $B_1$.

FIG. 10*a* shows the alignment of the magnetic field vectors in space at an instant relating to the time $t_0$. The illustration shows the vector of the fourth magnetic field $\Delta B_0$, produced by the auxiliary coils 42, 44, 46, 48, and which runs parallel to the Z axis. In this case, $\Delta B_0$ is the positive or negative excess of the magnetic field B above or below the resonant third magnetic field $B_0$, respectively, which is produced by the ferrite magnets 32, 44, 46, 48, points in the positive Z direction all the time, and is not illustrated in FIGS. 10*a* to 10*c*.

If only the magnetic field $B(t)=B_0$ acts initially, then the macroscopic magnetization of the tissue is aligned in the direction of the Z axis and the individual spins precess at the angular frequency $\omega_0$ about the Z axis. This means that the spins are initially stationary with respect to the rotating coordinate system X'Y'Z.

The third magnetic field $\Delta B_0$ and the alternating field $B_1$, which are superimposed to form the resultant magnetic field $B_R$, are now increased until the time $t=t_0$. The vector of the alternating field $B_1(t_0)$ points in the direction of the X' axis.

The alternating field $B_1$ oscillates linearly at the frequency $\omega_0$ essentially at right angles to the Z axis. Alternatively, the field $B_1$ may also rotate at the frequency $\omega_0$ about the Z axis. This is equivalent in terms of the projection in the X'-Z plane. Since the nucleus spins also rotate about the Z axis at the same frequency $\omega_0$, they are always in phase with the alternating field $B_1$.

Based on a classical interpretation, a resultant force F always acts on the magnetization or the spins in this arrangement, with this force F rotating the magnetization M or the spins in the X'-Z plane away from the Z axis. During this rotation, the spins essentially precess in phase. This rotation reduces the fourth magnetic field or modulation field $\Delta B_0$ to zero and then increases it further again continuously in the negative Z direction, in order to follow the change in the magnetization direction. This makes it possible to rotate the magnetization into the direction of the negative Z axis, that is to say to rotate the magnetization of the nuclei through 180°.

FIG. 10*b* shows the alignment of the magnetization M and of the various magnetic fields at a time $t_1$, which occurs later than $t_0$. The magnetization vector M has already been rotated to a considerable extent away from the Z axis.

In a corresponding manner, FIG. 10c shows an instant relating to a time $t_2$ which occurs even later than $t_1$.

Figure 11:
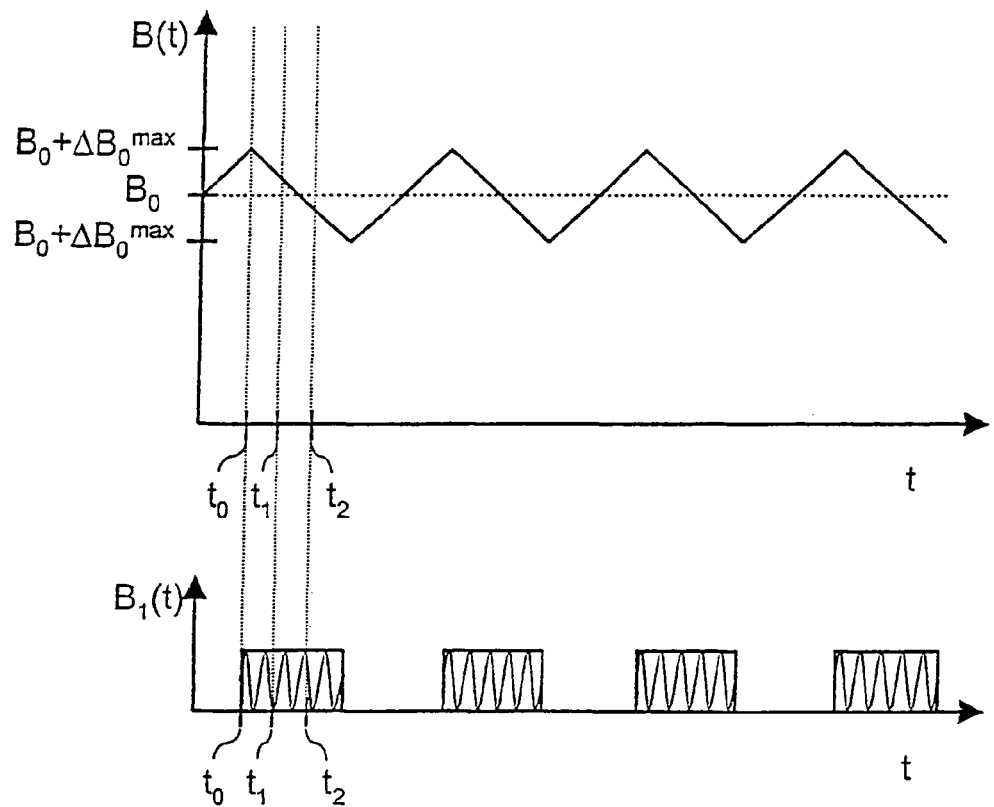
FIG. 11 shows a schematic illustration of the time profile of the first and second magnetic field.

In order to maximize the desired effect of motion simulation, the magnetization M should be rotated as frequently as possible. For this purpose, the auxiliary coil which produces the magnetic field $\Delta B_0$ is moved in a triangular shape, in a sawtooth shape or in a sinusoidal shape between $\Delta B_0^{max}$ and $-\Delta B_0^{max}$, that is to say symmetrically around zero. At the top, FIG. 11 shows schematically the most preferred triangular-waveform modulation of the first magnetic field B(t). The times $t_0$, $t_1$ and $t_2$ from FIGS. 10a to 10c are also shown. When the magnetic field B(t) is falling, the transmission coil and the alternating field $B_1$ are switched on in order to rotate the magnetization away from the positive Z axis, while the transmission coil is switched off when the field rises. In consequence, the alternating field $B_1(t)$ is amplitude-modulated with a square-waveform according to this exemplary embodiment. Other modulation forms for the first and/or second magnetic field, for example sinusoidal amplitude modulation, are, however, likewise within the scope of the invention. The blocks 50 which are shown at the bottom of FIG. 11 represent, schematically, the on-time of the alternating field $B_1$. During the off-time of the alternating field $B_1$, the spins relax, and the magnetization decreases again. The modulation period of the first and the fourth magnetic field is thus matched to the spin lattice relaxation time of the tissue, or at least corresponds to its order of magnitude. The period of the variation of the first magnetic field with time is preferably from one tenth to 10 times, in particular from once to 3 times or 5 times, the spin lattice relaxation time.

It is also within the scope of the invention for the falling flank of the modulation field $\Delta B_0$ to be made to be steeper than the rising flank, in order to achieve faster rotation.

The adiabatic run has been explained above by means of modulation of the first magnetic field B(t). The run can also be carried out analogously with a constant first magnetic field $B=B_0$ and a corresponding frequency change (so-called frequency sweep) of the alternating field $B_1$.

In addition, a receiving coil whose axis is in the Y direction detects the induced nuclear magnetic resonance signal, and is sensitive to its phase. The time integral of this signal is proportional to the total nuclear magnetic resonance effect, and is thus maximized.

One advantage of the adiabatic run is that the first magnetic field B may have up to about 10% inhomogeneity. This means that the method is several orders of magnitude less sensitive in this context than known methods, such as the spin echo method. The invention is also correspondingly insensitive to the angle between the first and second magnetic fields.

Figure 12:
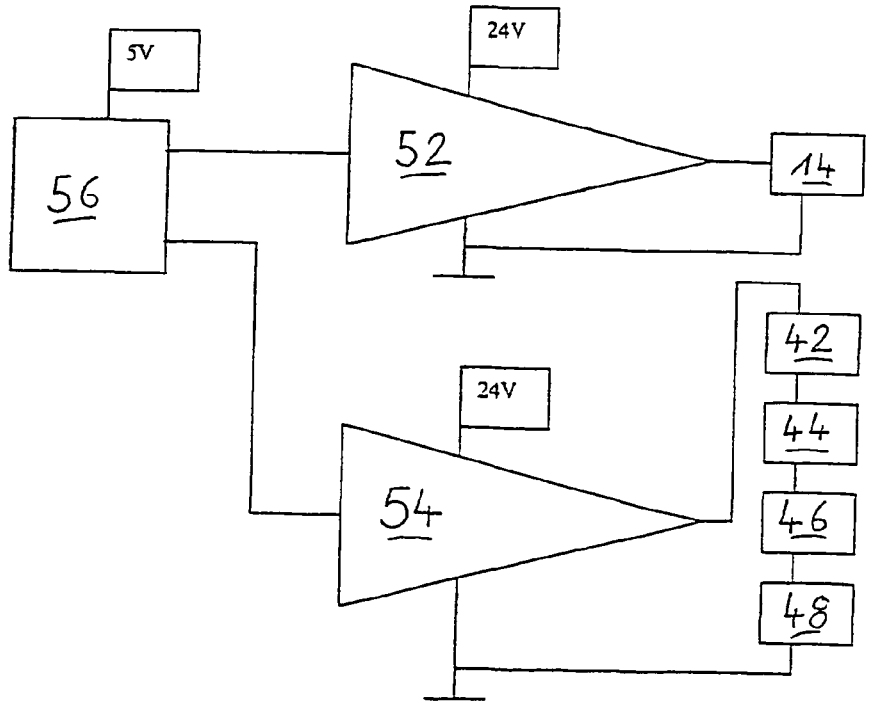
FIG. 12 shows a block diagram of the apparatus according to the invention with control electronics.

FIG. 12 shows an example of a circuit arrangement for the apparatus according to the invention, it respectively having an amplifier 52 and 54 for driving the transmission coil 14 and the auxiliary coils 42, 44, 46, 48. A control device or control logic 56 is associated with the transmission coil 14 and with the auxiliary coils 42, 44, 46, 48, as well as with the two amplifiers 52 and 54, and controls the modulation of the first and second magnetic fields.

Figure 13A:
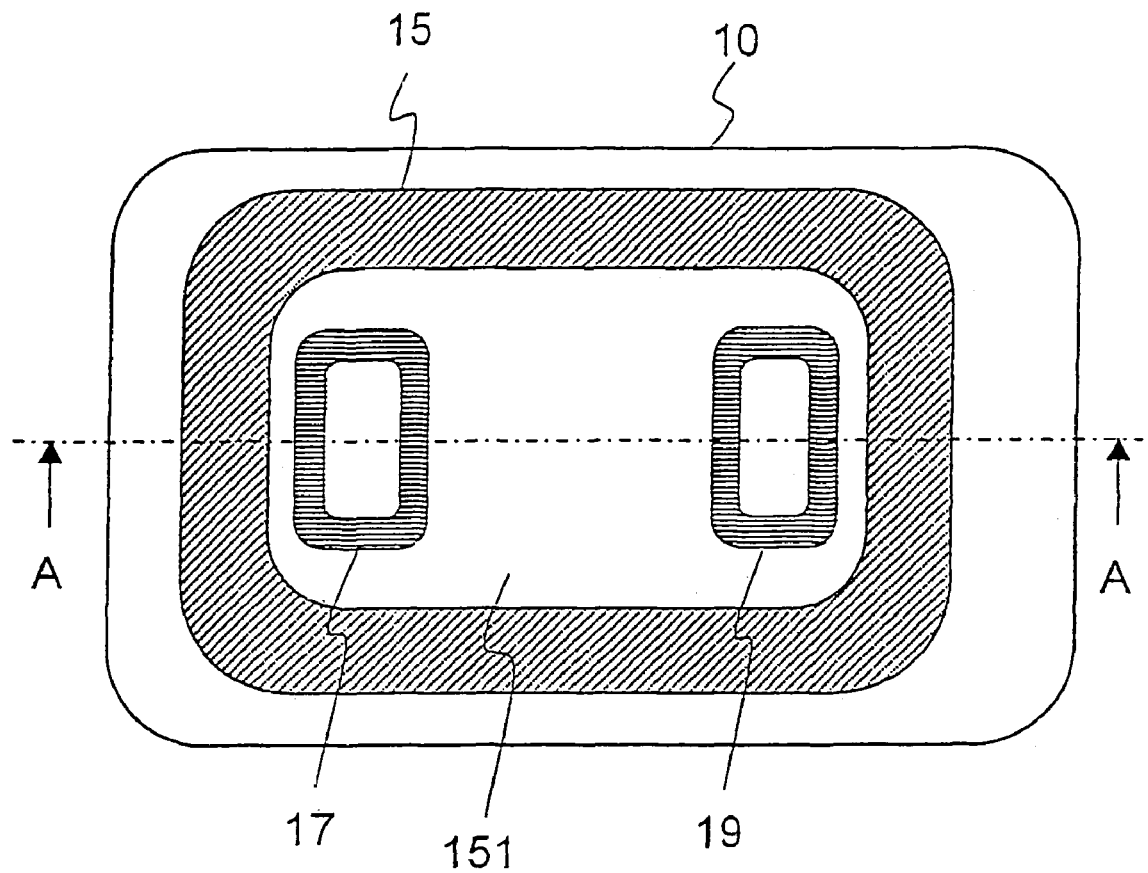
FIG. 13a shows a view of a second embodiment of the invention.
Figure 13B:
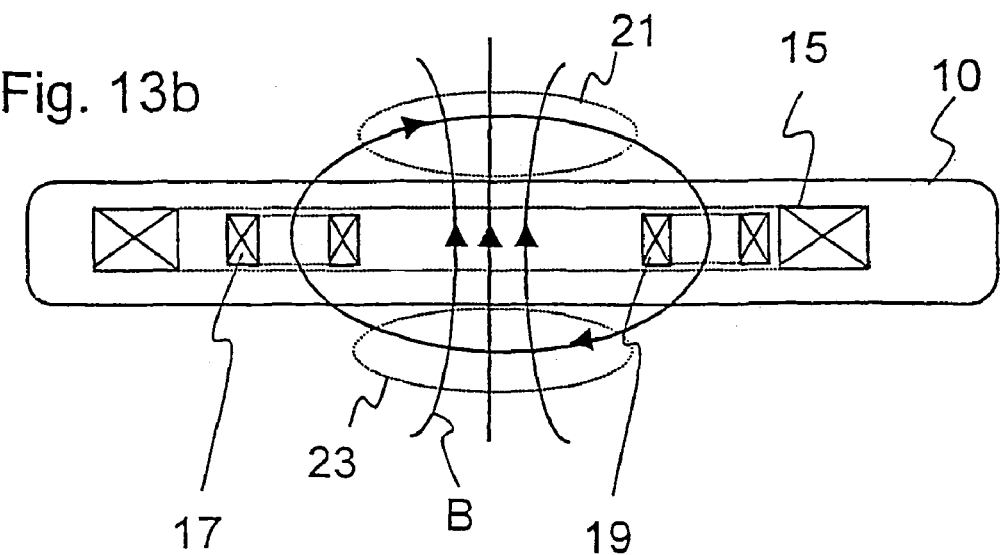
FIG. 13b shows a section drawing along the section line A-A in FIG. 13a, and FIG. 14 shows a block diagram of a circuit for controlling the coil in the second embodiment.

FIGS. 13a and 13b show a second embodiment of the invention. In this case, FIG. 13a shows a view of this second embodiment and FIG. 13b shows a section drawing along the section line A-A in FIG. 13a. The mat 10 has a flat toroidal coil 15 in whose inner area 151 two further flat toroidal coils 17 and 19 are arranged. In the same way as the embodiment which has been described with reference to FIGS. 1a and 1b, this embodiment is also suitable, for example, for implementing the 90° nuclear magnetic resonance signal pulsed method and the fast adiabatic nuclear magnetic resonance run.

The toroidal coil 15 produces a quasi-static magnetic field $B(t)=B_0+\Delta B_0(t)$. In order to achieve a wide treatment range, the magnitude of $\Delta B_0(t)$ is preferably half as much as $B_0$.

The flat toroidal coils 17 and 19 are operated in opposite senses, so that a north pole and a south pole respectively of the two coils point toward one face of the mat 10. In this way, these coils produce a magnetic field $B_1$ which, in the areas 21 and 23 above and below the mat 10, is essentially at right angles to the magnetic field B which is produced by the toroidal coil 15. When a patient is lying on the mat, then the tissue of the patient is located within this area 21. The area 21 thus defines a treatment area for the tissue to be treated.

The time profile of the magnetic field B(t) and of the magnetic field $B_1$ is in this case controlled as has been described above with reference to the further embodiments.

In contrast to the first embodiment of the invention, the magnetic field B in the treatment area runs approximately at right angles to the mat surface, however, or at right angles to the magnetic field B(t) produced by the coils 22, 24, 26, and 28 in the first embodiment. Furthermore, no fixed magnets are required for the second embodiment. The constant magnetic field component $B_0$ can in fact be produced by suitable operation of the toroidal coil 15, in the same way as the magnetic field $\Delta B_0$ which varies with time.

Figure 14:
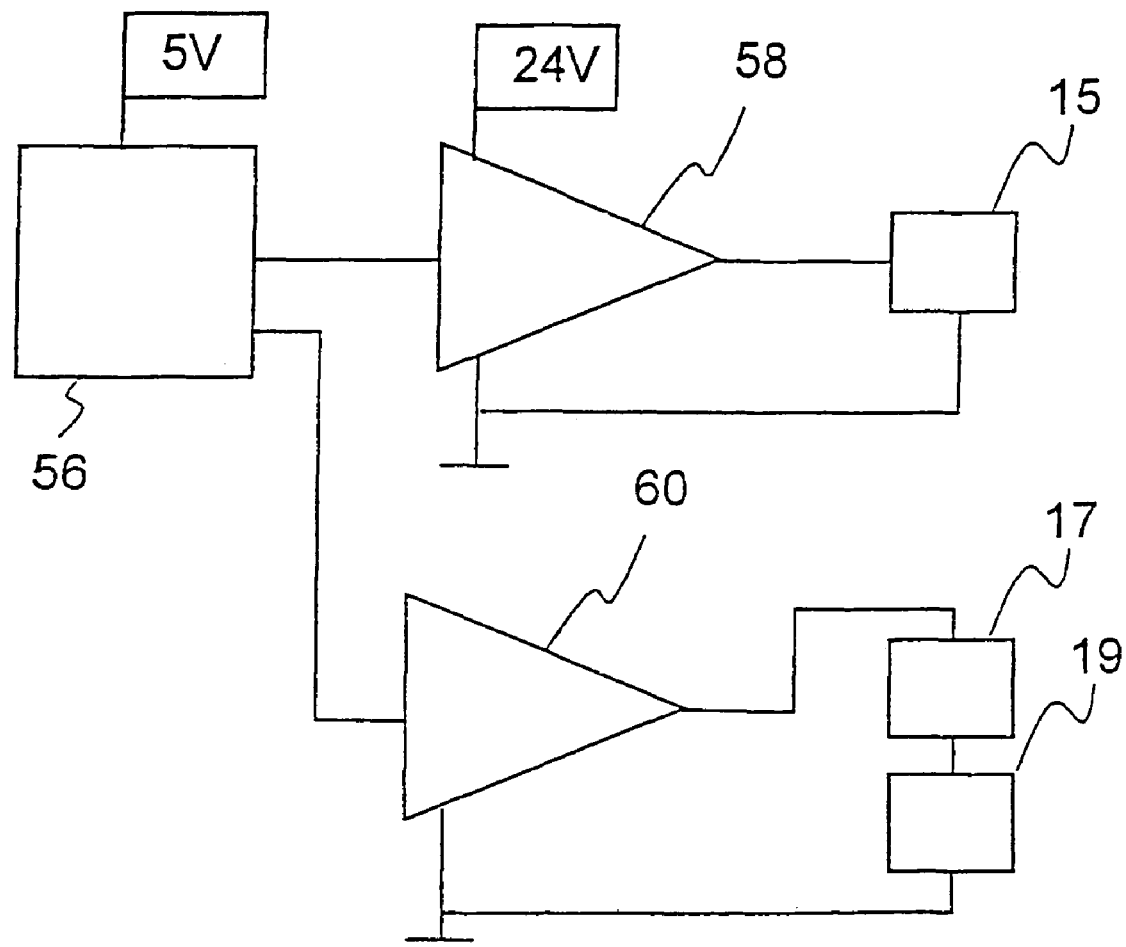

FIG. 14 shows, in the form of a block diagram, suitable control for the coils 15, 17 and 19 for producing a quasi-static magnetic field B(t), as well as an alternating field $B_1(t)$ with a time profile as illustrated, by way of example, in FIG. 11. In a similar way to the control illustrated in FIG. 12, the control has a logic circuit 56. The logic circuit 56 drives an amplifier 58 for driving the toroidal coil 15, as well as an amplifier for driving the toroidal coils 17 and 19 in order to produce the alternating field $B_1$. The amplifier 58 in this case produces a constant current for an embodiment without permanent magnets, which produces a constant magnetic field $B_0$ in the coil 15, as well as a current which is applied thereto, varies with time, and produces the variable magnetic field component $\Delta B_0$.

In summary, the present invention proposes a magnetic field therapy apparatus and a magnetic field therapy method which use the nuclear magnetic resonance signal as a motion sensor in order to stimulate the metabolism. The signal in this case simulates the motion of a body part. One advantageous feature in this case is that the proposed nuclear magnetic resonance therapy in all probability has no negative effects on the organism.

The nuclear magnetic resonance therapy apparatus according to the invention allows the magnetization to be rotated quickly and using little energy. The rotation is carried out, in particular, within one microsecond up to 30 seconds.

The invention claimed is:

1. An apparatus for treatment with magnetic fields, comprising:
   a first device for production of a first magnetic field,
   a second device for production of a second alternating magnetic field, with the first device and the second device forming an arrangement for production of nuclear magnetic resonance, wherein the second magnetic field runs essentially at right angles to the first magnetic field, and
   a mount with an upper face and a lower face, the mount being designed to be placed on body areas of a patient to be treated,
   wherein said second device comprises a coil having a coil axis that is disposed essentially at right angles to a surface of said mount, wherein said first device for production of said first magnetic field comprises at least two further coils being arranged adjacent to said coil of said second device for production of said second magnetic field, and wherein the first and second devices are arranged in a first plane, the upper face of the mount extends in a functional state essentially in a second plane, and the first plane runs essentially parallel to the second plane.

2. The apparatus as claimed in claim 1, wherein, in a treatment area above the upper face of the mount, the first magnetic field is disposed at an acute angle with respect to the upper face or the second magnetic field is disposed at an obtuse angle with respect to the upper face.

3. The apparatus as claimed in claim 1, wherein elements or compounds which are contained in the body areas to be treated have at least one spin resonance frequency in the first magnetic field, and the second magnetic field oscillates at least at times at a frequency which corresponds to the spin resonance frequency.

4. The apparatus as claimed in claim 1, wherein the first device comprises two or four coils between which the second device is substantially disposed.

5. The apparatus as claimed in claim 1, wherein the mount comprises a filling in which the first or second device is embedded.

6. The apparatus as claimed in claim 1, comprising a cushioned casing with an opening, which can be closed, for introduction or removal of the first or second device.

7. The apparatus as claimed in claim 1, wherein the mount is subdivided into a plurality of sections, and the mount can be folded between the plurality of sections.

8. The apparatus as claimed in claim 1, wherein the first device is designed to produce a magnetic field which varies with time.

9. The apparatus as claimed in claim 1, wherein the first device comprises at least one fixed magnet and at least one coil.

10. The apparatus as claimed in claim 1, wherein intensity or direction of the first magnetic field can be varied.

11. The apparatus as claimed in claim 1, wherein the mount is chosen from the group consisting essentially of a mat, a treatment couch, a treatment stool, a multi-winged arrangement which can be placed around a body part of a patient, leggings, a cover, and any combinations thereof.

* * * * *